United States Patent [19]

Ueda et al.

[11] Patent Number: 4,683,296
[45] Date of Patent: Jul. 28, 1987

[54] CARBAPENEM INTERMEDIATES

[75] Inventors: Yasutsugu Ueda, Manlius, N.Y.; Guy Roberge, St. Lambert, Canada

[73] Assignee: Bristol-Myers Company, New York, N.Y.

[21] Appl. No.: 725,594

[22] Filed: Apr. 22, 1985

Related U.S. Application Data

[63] Continuation-in-part of Ser. No. 472,443, Mar. 7, 1983.

[51] Int. Cl.$^4$ ............................................. C07C 113/00
[52] U.S. Cl. ................................... 539/558; 556/418; 540/350
[58] Field of Search ................... 534/558; 260/239 A; 556/418

[56] References Cited

U.S. PATENT DOCUMENTS 4,444,685  4/1984  Amato et al. .................. 556/418 X
4,525,582  6/1985  Amato et al. ...................... 554/558

FOREIGN PATENT DOCUMENTS 78026  5/1983  European Pat. Off. ........ 556/418 X

Primary Examiner—Paul F. Shaver
Attorney, Agent, or Firm—David M. Morse

[57] ABSTRACT

A new process is provided for preparing the key carbapenem intermediates of the formula

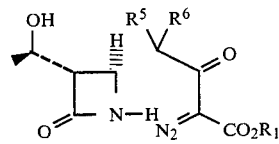

wherein $R^5$ and $R^6$ each independently represent hydrogen or methyl and $R_1$ represents a conventional carboxyl-protecting group.

3 Claims, No Drawings

CARBAPENEM INTERMEDIATES

CROSS-REFERENCE TO RELATED APPLICATIONS

This application is a continuation-in-part of our co-pending application Ser. No. 472,443 filed Mar. 7, 1983.

BACKGROUND OF THE INVENTION

1. Field of the Invention

The present invention is directed to a new process for producing a key intermediate used in the synthesis of thienamycin and other carbapenem antibiotics.

2. Description of the Prior Art

The antibiotic thienamycin of the formula

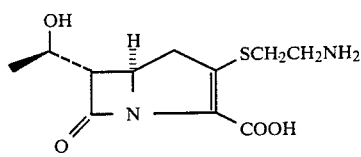

was originally obtained from fermentation of *Streptomyces cattleya* as described in U.S. Pat. No. 3,950,357. Thienamycin is an exceptionally potent broad-spectrum antibiotic which possesses notable activity against various Pseudomonas species, organisms which have been notoriously resistant to β-lactam antibiotics.

Because of the exceptional biological activity of thienamycin, a large number of derivatives have been prepared. While attempts have been made to synthesize derivatives with various substituents other than hydroxyethyl at the 6-position of the carbapenem ring system, the hydroxyethyl group is still considered the most advantageous 6-substituent for optimum activity.

Other derivatives have been made where the carbapenem nucleus is mono- or disubstituted at the 1-position, preferably with methyl (see, for example, European Patent Application No. 54,917).

Since fermentation procedures to prepare thienamycin and derivatives thereof have been unsatisfactory, several total synthesis procedures have been reported in the literature (see, for example, U.S. Pat. Nos. 4,287,123, 4,269,772, 4,282,148, 4,273,709, 4,290,947, and European Patent Application Nos. 7973 and 54,917). While the various synthetic procedures utilize different starting materials, they go through a common diazo intermediate having the formula

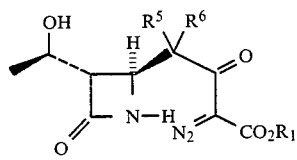

where $R^5$ and $R^6$ each independently represent hydrogen or methyl and $R_1$ represents a conventional carboxyl-protecting group. One of the most preferred carboxyl-protecting groups for intermediate I is the p-nitrobenzyl group which can be readily removed by catalytic hydrogenation after formation of the ultimate carbapenem product. Another most preferred protecting group is the allyl ester which can be readily removed with a catalyst comprising a mixture of a palladium compound and triphenylphosphine in an aprotic solvent such as tetrahydrofuran, diethyl ether or methylene chloride.

Recently attempts have been made to synthesize intermediate I (and subsequently thienamycin and other carbapenem derivatives) from readily available 6-APA. Karady et al., for example, in *J. Am. Chem. Soc.* 103(22): 6765–6767 (1981) disclose one such process which produces the diazo intermediate of the formula

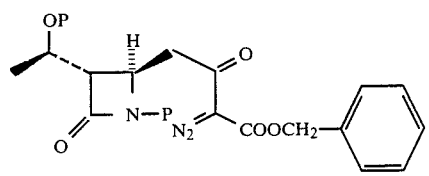

where P is t-butyldimethylsilyl by displacement of the O-protected azetidinone of the formula

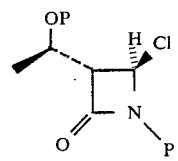

with an enol silyl ether of benzyl 2-diazoacetoacetate having the formula

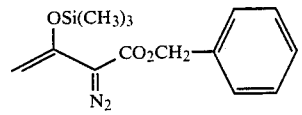

*Tetrahedron Lett.* 23(22): 2293–2296 (1982) discloses the preparation of the diazo intermediate of the formula

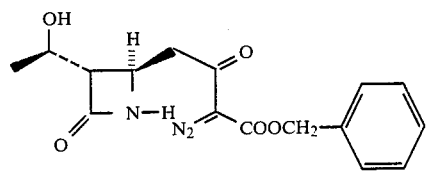

from 4-acetoxy-3-(1-hydroxyethyl)-2-azetidinone by Lewis acid catalyzed alkylation with the corresponding silyl enol ether of the formula

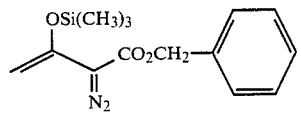

Yoshida et al. in *Chem. Pharm. Bull.* 29(10): 2899–2909 (1981) report another synthetic procedure for converting 6-APA to the O-protected azetidinone of the formula

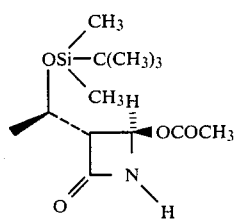

which can be converted to a diazo intermediate of Formula I by the process disclosed in the above-mentioned *Tetrahedron Lett.* reference.

Since the diazo intermediates of Formula I are preferred carbapenem intermediates, it would be desirable to have a process for converting readily available azetidinone compounds of the general formula

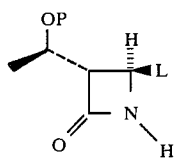

where L is a conventional leaving group such as halo or acetoxy and P is a conventional hydroxyl-protecting group such as triorganosilyl to the corresponding ester intermediates of Formula I.

Since the Lewis acid catalyzed alkylation of ketones as their silyl enol ethers has been described in the literature (see, for example, *Tetrahedron Lett.* 23(22): 2293–2296, 1982 and also *Tetrahedron Lett.* 23(4): 379–382, 1982), it might be expected that the desired ester intermediate I or a hydroxy-protected derivative thereof could be prepared by Lewis acid catalyzed alkylation of an appropriate azetidinone compound II with an enol silyl ether of the diazoacetoacetate ester having the formula

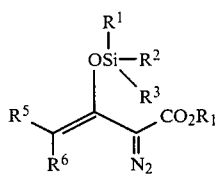

wherein $R^5$ and $R^6$ are each independently hydrogen or methyl, $R_1$ is a conventional carboxyl-protecting group and $R^1$, $R^2$, and $R^3$ are each independently $C_1$–$C_4$ alkyl or, alternatively

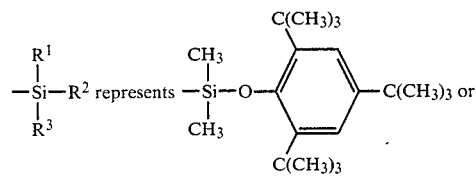

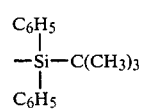

Unfortunately, however, the present inventors have found that the known method of preparing compounds of Formula III does not work when a p-nitrobenzyl protecting group is desired or when the tert-butyldimethylsilyl hydroxyl protecting group is employed. Thus, the prior art method for preparing enol silyl ethers of diazoacetoacetates employs silylation of a diazoacetoacetate ester of the formula

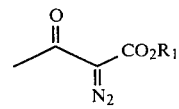

wherein $R_1$ is a carboxyl-protecting group to the enol silyl ether ester

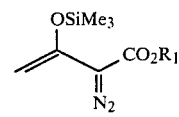

by use of a trimethylsilyl halide silylating agent in the presence of a strong base, e.g. trimethylchlorosilane with a lithium base such as lithium hexamethyldisilazide. When this prior art method is employed with the p-nitrobenzyl ester

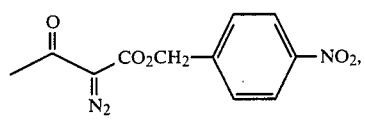

the strong base needed to form the enolate is incompatible with the p-nitrobenzyl ester because of the highly reactive methylene group. Use of weaker organic bases such as trialkylamines with the triorganosilyl halide silylating agent, however, does not produce the desired enol silyl ester. Additionally, the prior art procedure which generally allows preparation of trimethylsilylenolethers of the type

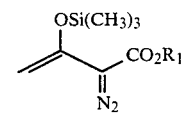

where $R_1$ is a conventional ester protecting group other than a highly reactive ester such as p-nitrobenzyl, was not successful for preparation of the corresponding tert-butyldimethylsilylenolethers which, as pointed out below, are particularly preferred carbapenem intermediates.

It was the object of the present invention to provide a novel and general silylation procedure which would be applicable for producing silylenolethers of the formula

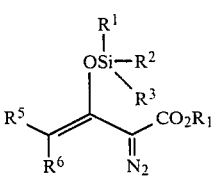

where $R^5$ and $R^6$ are each independently hydrogen or methyl, $R_1$ is a conventional carboxyl-protecting group and $R_1$, $R^2$, and $R^3$ are each independently $C_1$-$C_4$ alkyl or, alternatively,

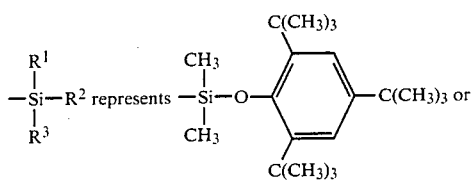

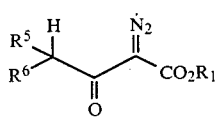

from the intermediate

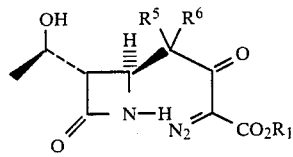   IVA wherein $R^5$, $R^6$, and $R_1$ are as defined above.

Successful preparation of intermediate III would then allow preparation of the key carbapenem intermediate

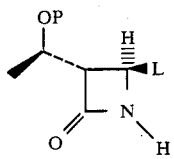   I or a hydroxyl-protected derivative thereof by reaction of intermediate IIIA with a suitable O-protected azetidinone of the formula

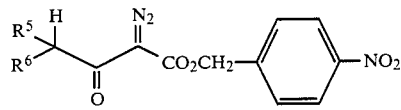   II wherein P and L are as defined above followed by removal, if desired, of the hydroxyl-protecting group.

DETAILED DESCRIPTION

The present invention is based on the unexpected discovery that the p-nitrobenzyl diazoacetoacetate intermediate of the formula

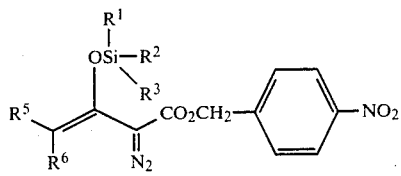   IV' wherein $R^5$ and $R^6$ are each independently hydrogen or methyl could be successfully converted to the corresponding enol silyl ether intermediate of the formula

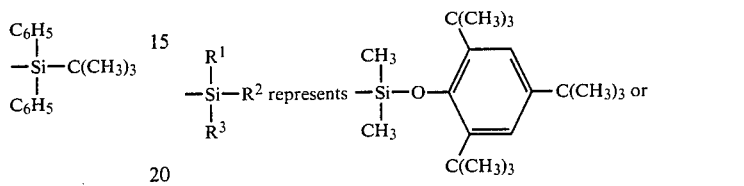   III' wherein $R^5$ and $R^6$ are as defined above and $R^1$, $R^2$, and $R^3$ are each independently $C_1$-$C_4$ alkyl or, alternatively,

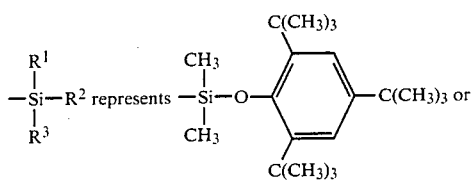

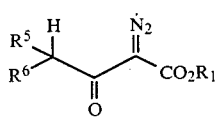

by reaction of compound IV' with a triorganosilyl triflate silylating agent of the formula

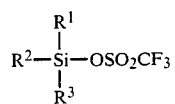   V wherein $R^1$, $R^2$, and $R^3$ are as defined above in an inert organic solvent and in the presence of an organic base. Use of the silyl triflate silylating agent instead of the prior art silylchloride reagent allows use of an organic base such as a trialkylamine [e.g. tri($C_1$-$C_4$)alkylamine] instead of the prior art strong bases, thus making it possible to successfully form the desired silyl enol ether intermediate III' in high yield despite the presence of the highly reactive methylene group in the p-nitrobenzyl moiety.

The reaction of intermediate IV' with the triorganosilyl triflate silylating agent is carried out in an inert organic solvent such as methylene chloride, tetrahydrofuran, carbon tetrachloride, dioxane, dimethoxyethane, diethyl ether or chloroform at a temperature in the range of from about −40° C. to +30° C. Most conveniently the reaction is allowed to take place at a temperature in the range of about 0°-5° C.

The triorganosilyl triflate may be any trialkyl ($C_1$-$C_4$ alkyl) silyl trifluoromethylsulfonate such as trimethylsilyl trifluoromethylsulfonate, tri-isopropylsilyl trifluoromethylsulfonate, triethylsilyl trifluoromethylsulfonate, or tert-butyldimethylsilyl trifluoromethylsulfonate or it may be tert-butyldiphenylsilyl trifluoromethylsulfonate or 2,4,6,-tri(t-butylphenoxy)dimethyl-silyl trifluoromethylsulfonate. The most preferred silylating agent is tert-butyl dimethylsilyl trifluoromethylsulfonate.

Organic amine bases such as diisopropylethylamine, DBU (1,8-diazabicyclo[5.4.0]undec-7-ene), DBN (1,5-diazabicyclo-[4.3.0]non-5-ene) and especially tri($C_1$-$C_4$)alkylamines (e.g. trimethylamine, triethylamine, tributylamine, tripropylamine) are suitable for use with the triorganosilyl triflate silylating agent.

Generally the organic base, triorganosilyl triflate and intermediate IV' are reacted in approximately equimolar amounts with the base being used in slight excess. The most preferred molar ratio of intermediate IV':triorganosilyl triflate:base is about 1:1.2:1.4.

The first compounds prepared of formula III' were the trimethylsilylenolethers. While readily prepared in high yields by the above-described process, these intermediates were somewhat labile and hydrolyzed to the p-nitrobenzyl α-diazoacetoacetates on contact with water or simply atmospheric pressure, thus creating difficulty in handling. To overcome this problem, the corresponding tert-butyldimethylsilylenolethers were prepared by using tert-butyldimethylsilyl trifluoromethanesulfonate in place of trimethylsilyl trifluoromethanesulfonate. In contrast to the trimethylsilylenolethers, the tert-butyl dimethylsilylenolethers were much more stable to neutral water, thus permitting aqueous workup. The compound, p-nitrobenzyl 2-diazo-3-(tert-butyl dimethylsilyloxy)-3-butenoate, for example, has been stored in a capped bottle in a refrigerator (0°–5° C.) for more than one year without any hydrolysis to the diazoacetoacetate.

The process described above for preparation of silylenolethers of the p-nitrobenzyl ester of α-diazoacetoacetates was found to be quite general for a wide variety of α-diazoacetoacetate esters. Thus, in its broadest aspect the present invention provides enol silyl ether intermediates of the formula

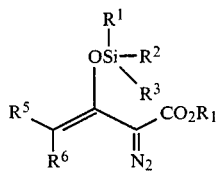

IIIA wherein $R^5$ and $R^6$ are each independently hydrogen or methyl, $R^1$, $R^2$, and $R^3$ are each independently $C_1$–$C_4$ alkyl or, alternatively,

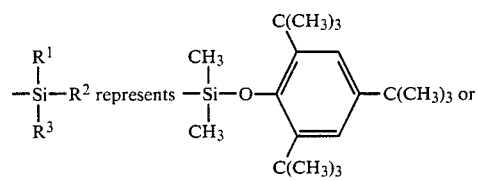

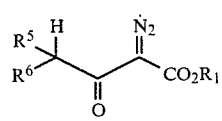

and $R_1$ represents a conventional ester protecting group for a carboxylic acid, by reaction of a compound of the formula

IVA $$R^5\underset{R^6}{\overset{H}{\diagdown}}\underset{\underset{O}{\|}}{C}\underset{}{\overset{N_2}{\|}}CO_2R_1$$

wherein $R^5$, $R^6$, and $R_1$ are as defined above with a triorganosilyl triflate silylating agent of the formula

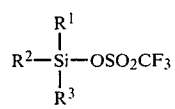

V wherein $R^1$, $R^2$, and $R^3$ are as defined above in an inert organic solvent and in the presence of an organic base. The conditions for this reaction are as described above in connection with the preparation of compounds III'.

A preferred embodiment of the present invention comprises the novel compounds of the formula

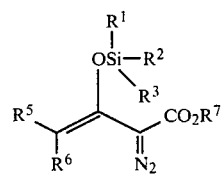

III wherein $R^5$ and $R^6$ are each independently hydrogen or methyl, $R^7$ is an ester group selected from $C_1$–$C_4$ alkyl, p-nitrobenzyl, —$CH_2CH$=$CH_2$, —$CH_2CH$=$CHC_6H_5$, —$CH_2CH$=$CHCO_2CH_3$,

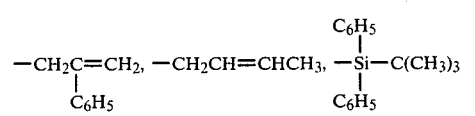

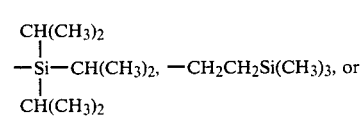

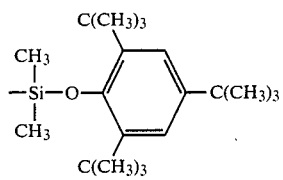

and $R^1$, $R^2$ and $R^3$ are each independently $C_1$–$C_4$ alkyl or, alternatively,

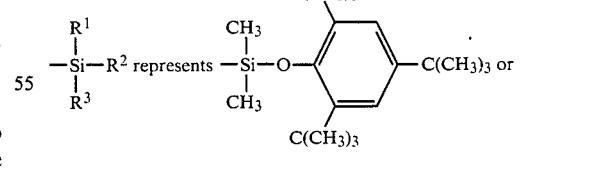

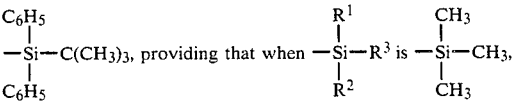

$R^7$ may not be allyl or $C_1$–$C_4$ alkyl, and the process for their preparation.

Another preferred embodiment comprises the compounds of the formula

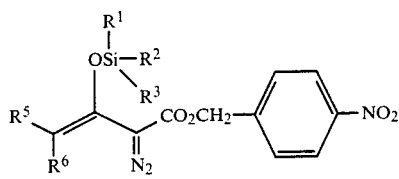                                           III' wherein $R^5$ and $R^6$ are each independently hydrogen or methyl and $R^1$, $R^2$, and $R^3$ are each independently $C_1$–$C_4$ alkyl or, alternatively,

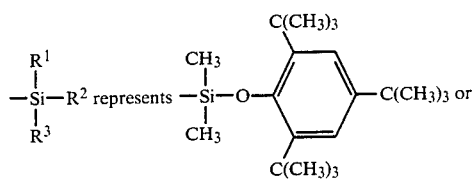

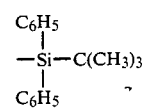

Another preferred embodiment comprises the compounds of the formula

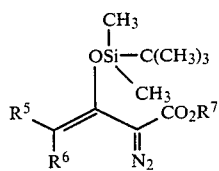

wherein $R^5$ and $R^6$ are each independently hydrogen or methyl, and $R^7$ is an ester group selected from $C_1$–$C_4$ alkyl, p-nitrobenzyl,

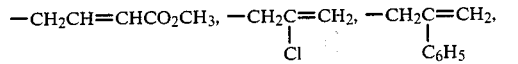

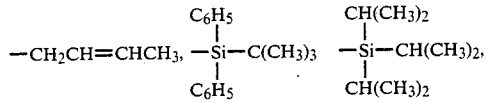

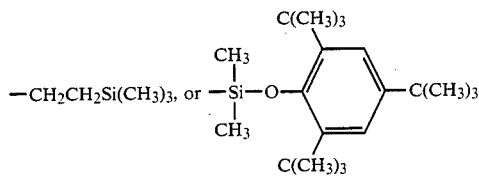

Within the above-described preferred embodiments, $R^5$ and $R^6$ are preferably both hydrogen or one of $R^5$ and $R^6$ is hydrogen and the other is methyl.

Once intermediates of Formula III are prepared, they may be used in a further aspect of the present invention to prepare the known diazo intermediate

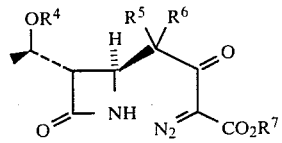                                           IA wherein $R^4$ is hydrogen or a conventional hydroxyl-protecting group and $R^5$, $R^6$, and $R^7$ are as defined above. Thus, intermediate III is reacted with a suitable O-protected azetidinone of the formula

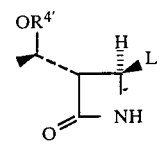                                           IIA wherein L is a conventional leaving group and $R^{4'}$ is a conventional hydroxyl-protecting group in an inert organic solvent and in the presence of a Lewis acid catalyst and if desired, the hydroxyl-protecting group is removed to obtain the corresponding hydroxyethyl intermediate. Examples of suitable inert organic solvents are methylene chloride, chloroform, carbon tetrachloride, dioxane, diethyl ether, tetrahydrofuran or dimethoxyethane. Suitable Lewis acid catalysts include zinc chloride, zinc iodide, zinc bromide, titanium tetrachloride, magnesium bromide, boron trifluoride, aluminum chloride, stannic chloride trimethyltrifluoromethylsulfonate (TMF.OTf), and ferric chloride. A preferred solvent is methylene chloride and a preferred catalyst is zinc chloride.

Azetidinone compounds of Formula IIA are known compounds or may be prepared by known methods. The hydroxyalkyl group of such compounds is protected by a conventional hydroxy-protecting group. While the particular protecting group used is not critical and may be selected from a large number of such groups known in the art, it is preferred to use a triorganosilyl protecting group such as trimethylsilyl or tert-butyl dimethylsilyl since such groups are readily removable by treatment with methanolic HCl or with fluoride ion (e.g. tetra-n-butyl ammonium fluoride/tetrahydrofuran). Other examples of suitable hydroxy-protecting groups include p-nitrobenzyloxycarbonyl which can be removed by catalytic hydrogenation, allyloxycarbonyl which can be removed by Pd(P$\phi_3$)$_4$-catalyzed reaction and 2-trihaloethoxycarbonyl (—CO$_2$CH$_2$CX$_3$ where X=Cl or Br) which may be removed by treatment with Zn-acetic acid in methanol. The leaving group L may be any conventional leaving group such as halo (e.g. chloro) or acyloxy (e.g. acetoxy, propionyloxy or t-butyryloxy) but is most preferably acetoxy. Generally it is preferred to add an excess of the silyl enol ether III to the azetidinone II.

Following the alkylation reaction to form the hydroxyl-protected diazo intermediate, the protecting group may be subsequently removed by known methods so as to provide the desired intermediate IA. Triorganosilyl protecting groups, as mentioned above, are especially preferred because they may be readily removed without disruption of the remaining portion of the molecule.

Diazo intermediate IA may be converted by known methods to thienamycin and various other carbapenem derivatives having useful antibacterial activity.

The following examples illustrate but do not limit the scope of the present invention. Melting points were determined on a Gallenkamp melting point apparatus and are not corrected. The infrared spectra were recorded on a Perkin-Elmer 267 Grating Infrared Spectrometer. The $^1$H nuclear magnetic resonance spectra were taken with either the Varian EM-360 (60 MHz), unless specified, or a Varian CFT-20 (80 MHz) NMR spectrometer. Tetramethylsilane was used as an internal standard and chemical shifts are reported in parts per million ($\delta$) relative to the internal standard. The ultraviolet spectra were recorded on a Unicam SP8-100 uv spectrometer. Optical rotations were measured with a Perkin-Elmer Model 141 polarimeter. Tetrahydrofuran was freshly distilled from lithium aluminum hydride. Anhydrous diethyl ether (Fisher) was used without further treatment. All other solvents were reagent grade and had been stored over molecular sieves before use. Triethylamine and tetramethylethylenediamine were distilled from $CaH_2$ and stored over NaOH. Anhydrous zinc chloride was fused under a reduced pressure and pulverized prior to use. Allyl diazoacetoacetate and ethyl diazoacetoacetate were prepared by the general procedure of Regitz*. Analytical thin layer chromatography (tlc) was conducted on precoated plates (Silica Gel 60F-254, E. Merck). Visualization was affected by uv light, iodine or Ammonium molybdate (VI). Preparative layer chromatography (plc) was performed on silica gel plates prepared from Silica Gel 60 GF-254 (E. Merck). For column chromatography, 70–230 mesh silica Gel 60 (E. Merck) was used.

*(a) M. Regitz and A. Liedhegener, *Chem. Ber.* 99: 3128 (1966);

(b) M. Regitz, *Angew. Chem.* 79: 786 (1967); (c) M. Regitz, *Synthesis:* 351 (1972).

PREPARATION OF STARTING MATERIALS

Preparation 1 p-Nitrobenzyl acetoacetate

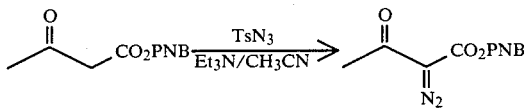

A mixture of ethyl acetoacetate (140 g, 1.08 mole) and p-nitrobenzyl alcohol (153 g, 1.00 mole; was washed with diethyl ether prior to use) in toluene (1 L) was slowly distilled, 900 ml of the solvent being collected over a period of 15 hours. After cooling, any insoluble material was removed by filtration over Celite, washed with toluene and evaporated in vacuo to obtain 280 g of a crude oil. This oil was crystallized at 5° C. from diethyl ether (280 ml) to yield 181.55 g (0.766 mole, 76.6% yield) of the title compound as off-white crystals: mp 40°–42° C.; ir (film) $\nu_{max}$: 1740 (ester), 1715 (C=O), 1515 and 1345 ($NO_2$) cm$^{-1}$; $^1$Hmr (CDCl$_3$) $\delta$: 1.98 (s, impurity), 2.32 (3H, s, CH$_3$), 3.62 (2H, s, —COCH$_2$CO$_2$R), 5.08 (s, impurity), 5.28 (2H, s, —CO$\underline{_2$CH$_2}$Ar), 7.53 (2H, "d", J=9 Hz, ArH's), and 8.23 ppm (2H, "d", J=9 Hz, ArH's); Rf 0.45 (diethyl ether). An analytical sample was obtained by recrystallization from toluene-hexanes: mp 47°–49° C.

Anal. calc'd for $C_{11}H_{11}NO_5$: C, 55.70; H, 4.67; N, 5.91. Found: C, 55.59; H, 4.62; N, 5.85.

Preparation 2

Trimethylsilyl acetoacetate

A solution of ethyl acetoacetate (2.60 g. 20 mmol; Aldrich) and trimethylsilylethanol (2.51 g, 21.1 mmol, Fluka) in toluene (100 ml) was heated and slowly distilled at 80°–100° with a Vigreaux column (1.7 cm×7 cm), removing most of the solvent over a period of 10 h. The residue was distilled under a reduced pressure with a Vigreaux column (1.7 cm×7 cm to obtain 3.34 g (16.5 mmol, yield 82.7%) of the title compound as a colourless oil: Rf 0.32 (20% ETOAc/Hex); bp 85°–88° C. (0.3 Torr); ir (neat) $_{max}$: 1740 (ketone) and 1720 (ester) cm$^{-1}$; $^1$Hmr (CDCl$_3$) : 0.07 (9H, s, SiMe$_3$), 1.00 (2H, 't' J=8 Hz, SiCH$_2$), 1.93 (0.45H, s, MeC(OH)=), 2.28 (2.55H, s, MeCO), 3.12 (0.15H, s, OH of the enol form), 3.43 (1.7H, s, COCH$_2$), 4.2 (2H, 't' J=8 Hz, CO$_2$CH$_2$), and 4.95 (0.15H, s, vinyl proton of the enol form) ppm;

Anal. calc. for $C_9H_{18}O_3Si$: C 53.43, H 8.97; found: C 53.19, H 8.82.

Preparation 3 p-Nitrobenzyl 2-diazo-3-ketobutoate

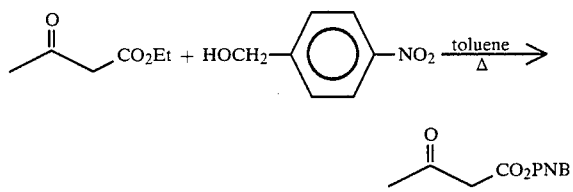

To a solution of p-nitrobenzyl acetoacetate (134.6 g, 0.568 mole) and triethylamine (79.0 ml, 0.568 mole) in CH$_3$CN (340 ml) was added at 0°–5° C. under a nitrogen atmosphere p-toluenesulfonyl azide (130 g, 0.639 mole; 97% pure) over a period of 15 minutes. During this period the title compound started precipitating. The cooling bath was removed and the mixture was stirred at room temperature for 3 hours. The mixture was cooled in an ice-bath for 30 minutes and the precipitate was filtered, washed with cold CH$_3$CN (75 ml) and then cold diethyl ether (200 ml), and dried to yield 135.06 g (0.514 mole, yield 90.4%) of the title compound as pale yellow powder: $^1$Hmr (CDCl$_3$) $\delta$: 2.50 (3H, s, —CH$_3$), 5.38 (2H, s, —CO$_2$CH$_2$Ar), 7.53 (2H, "d", J=9 Hz, aromatic Hs) and 8.27 ppm (2H, "d", J=9 Hz, aromatic Hs); ir (CH$_2$Cl$_2$) $\nu_{max}$: 2130 (N$_2$), 1720 (ester), 1655 (C=O) 1520 and 1350 cm$^{-1}$ (NO$_2$); Rf 0.65 (ethyl acetate).

Preparation 4

2-Trimethylsilylethyl α-diazoacetoacetate

To a solution of trimethylsilylethyl acetoacetate (10.6 g, 50.0 mmol) and triethylamine (7.10 mL, 51.5 mmol) in acetonitrile (85 mL) was added in an ice-bath p-toluenesulfonyl azide (10.0 g, 50.7 mmol) and the reaction mixture stirred at room temperature for 20 h. After evaporation of the solvent in vacuo, the residue was extracted with Et$_2$O (90 mL) and this extract was washed with a solution of KOH (3.0 g) in H$_2$O (83 mL) and again a solution of KOH (0.9 g) in H$_2$O (30 mL), then brine, and dried (Na$_2$SO$_4$). Evaporation of the solvent in vacuo gave 11.6 g of a crude oil which was purified by column chromatography (SiO$_2$, 150 g) eluting with 20% EtOAc/Hexanes, to obtain 9.65 g (42.3 mmol, yield 84.5%) of the title compound as yellowish oil: Rf 0.44 (20% EtOAc/Hex); ir (neat)$\nu_{max}$: 2130 (C=N$_2$), 1715 (ester), and 1660 (ketone) cm$^{-1}$; uv (CH$_2$Cl$_2$)$\lambda_{max}$: 257 nm ($\epsilon$7200); $^1$Hmr (CDCl$_3$)$\delta$: 0.07 (9H, s, SiMe$_3$), 1.03 (2H, 't' J=8 Hz, CH$_2$Si), 2.47 (3H, s, COCH$_3$), and 4.30 (2H, 't' J=8 Hz, CO$_2$CH$_2$ ppm.

Preparation 5 p-Nitrobenzyl-2-diazo-3-oxo-n-valerate

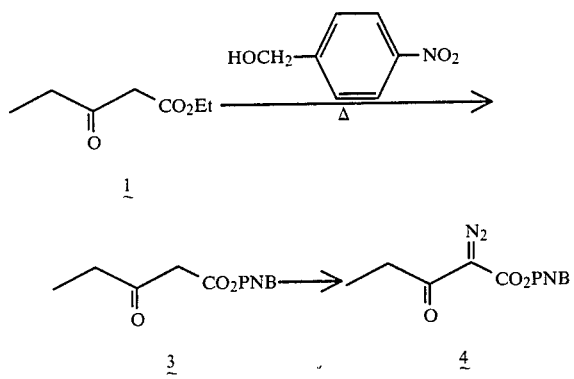

A solution of 50 g (0.35M) of ethyl 3-oxo-n-valerate and 54 g (0.35M) of p-nitrobenzyl alcohol in 400 ml of toluene was heated at 130°-140° without a refluxing condenser for 18 h. Evaporation of solvent gave a yellow crystalline material which was recrystallized from Et$_2$O-pentane to produce 75 g (86% yield) of p-nitrobenzyl 3-oxo-n-valerate (3). m.p. 33°-34°. IR (KBr) $\gamma$ 1740 and 1705 cm$^{-1}$. NMR (CDCl$_3$) $\delta$ 1.20(3H, t, J=7.0 Hz), 2.65(2H, q, J=7.0 Hz), 3.60(2H, s), 5.28(2H, s), 7.45(2H, d, J=9.5 Hz), and 8.18(2H, d, J=9.5 Hz). To a solution of 55.5 g. (0.22M) of compound 3 in 500 ml of CH$_3$CN was added at 0°45 g (0.44M) of TEA followed by 50 g (0.22M) of p-carboxybenzenesulfonyl azide. The ice bath was removed and the mixture was allowed to stir for 90 min. The precipitate was filtered, washed with CH$_3$CN and the filtrate was concentrated to $^{ca}$ 100 ml volume and diluted with 800 ml of EtOAc. The organic solution was washed with aq. NaHCO$_3$, brine and dried (MgSO$_4$). Evaporation of the dried solvent gave 55 g (90% yield) of compound 4 as a slightly yellow crystals. m.p. 96°-97°. IR (KBr) $\gamma$ 2120 and 1710 cm$^{-1}$. NMR (CDCl$_3$) $\delta$ 1.20(3H, t, J=7.0 Hz), 2.85(2H, q, J=7.0 Hz), 5.40(2H, s), 7.50(2H, d, J=8.0 Hz), and 8.15(2H, d, J=8.0 Hz).

Preparation 6

Allyl diazoacetoacetate

A. Allyl acetoacetate

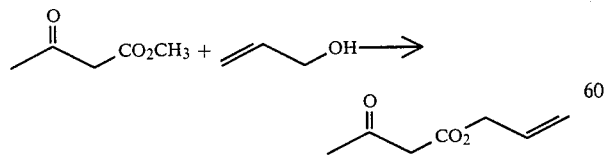

In a 2 l flask equipped with a magnetic stirrer, equipped for a Vigreaux column for distillation, a heating mantle and N$_2$, there was added 4.0 mole (432 ml) of methyl acetoacetate and 8.0 mole (464.6 g) of allyl alcohol. The reaction mixture was distilled for 12 hours at 92° C. There was added 136 ml (2.0 mole) of allyl alcohol and the mixture was distilled 23 hours. There was then added 136 ml (2.0 mole) of allyl alcohol and the mixture was distilled 16 hours. The reaction mixture was then distilled under vacuum and product was collected at 105°-110° C./35 mm Hg. There was obtained 414 g of allyl acetoacetate (73% yield).

B. Allyl diazoacetoacetate

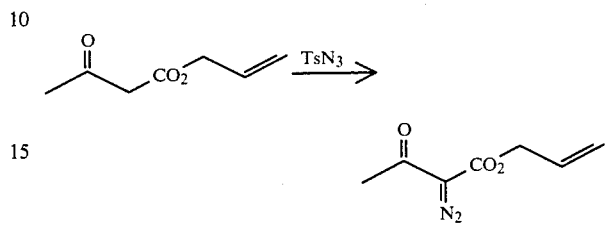

To a solution of allyl acetoacetate (226.5 g, 1.594 mole) in 3 l acetonitrile and triethylamine (243.4 ml, 1.753 mole), there was added p-toluenesulfonyl azide (345.3 ml, 1.753 mole) over a 1 hour period while keeping the temperature at ~20° C. with a cooling bath. The reaction mixture became yellow. The reaction mixture was then stirred at room temperature under a nitrogen atmosphere for 18 hours. The mixture was concentrated on a rotary evaporator. The residue was dissolved in diethyl ether (2.6 l) and 1M aqueous KOH (800 ml). The organic phase was washed five times with 1M KOH (500 ml) and once with brine (400 ml). After drying over MgSO$_4$ and concentration on a rotary evaporator (temp. $\leq$30° C.), there was obtained 260.2 g (97%) of the title product.

Following the general procedures described above, the following starting materials may be prepared:

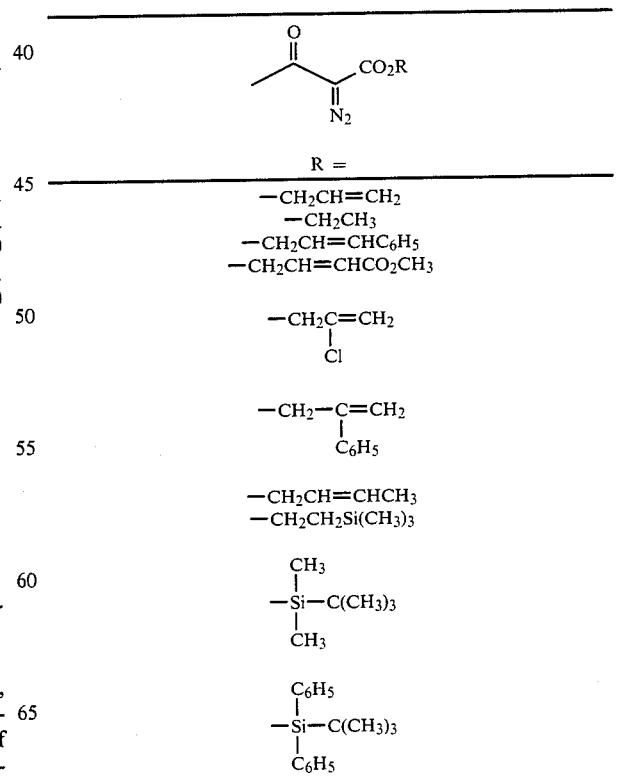

R =

—CH$_2$CH=CH$_2$
—CH$_2$CH$_3$
—CH$_2$CH=CHC$_6$H$_5$
—CH$_2$CH=CHCO$_2$CH$_3$

—CH$_2$C=CH$_2$
    |
    Cl

—CH$_2$—C=CH$_2$
        |
        C$_6$H$_5$

—CH$_2$CH=CHCH$_3$
—CH$_2$CH$_2$Si(CH$_3$)$_3$

CH$_3$
    |
—Si—C(CH$_3$)$_3$
    |
    CH$_3$

C$_6$H$_5$
    |
—Si—C(CH$_3$)$_3$
    |
    C$_6$H$_5$

-continued

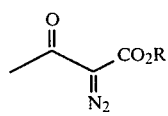

R =

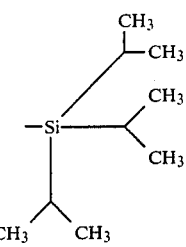

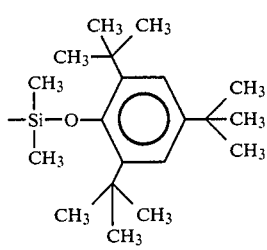

EXAMPLE 1

Preparation of p-Nitrobenzyl
2-diazo-3-trimethylsilyloxy-3-butenoate

To a suspension of p-nitrobenzyl α-diazoacetoacetate (236 mg, 1 mmole) and triethylamine (0.15 ml, 1.08 mmole) in CH$_2$Cl$_2$ (2 ml) was added at 0°–5° C. trimethylsilyl trifluoromethylsulfonate (0.22 ml) under a nitrogen atmosphere and the mixture was stirred for 30 minutes. To this clear yellow solution was added dry hexanes (30 ml) and the reaction mixture was stirred for 10 minutes. After removing the oily deposit, the hexanes solution was evaporated in vacuo to yield yellow solid which was redissolved in dry hexanes (50 ml). The insoluble material was filtered over Celite and the filtrate was evaporated in vacuo to obtain 277 mg (0.90 mmole, yield 90%) of the title compound as yellow crystals: ir (film) $\nu_{max}$: 2100 (N$_2$), 1705 (ester), 1520 and 1345 cm$^{-1}$ (NO$_2$); $^1$Hmr (CDCl$_3$) δ: 0.27 (9H, s, —SiMe$_3$), 4.23 (1H, d, J=2 Hz, vinyl proton), 4.93 (1H, d, J=2 Hz, vinyl proton), 5.32 (2H, s, —CO$_2$CH$_2$Ar), 7.48 (2H, "d", J=9 Hz, aromatic protons) and 8.23 ppm (2H, "d", J=9 Hz, aromatic protons).

EXAMPLE 2

Preparation of p-Nitrobenzyl 2-diazo-3-tert-butyl dimethylsilyloxy-3-butenoate

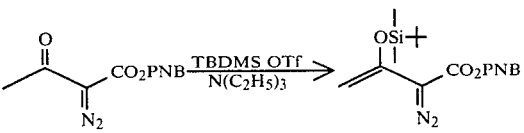

To a suspension of p-nitrobenzyl α-diazoacetoacetate (26.30 g, 0.10 mole) and triethylamine (14.57 g, 20.00 ml, 0.14 mole) in dry methylene chloride (200 ml) was added at 2° C. tert-butyl dimethylsilyl trifluoromethylsulfonate (31.72 g, 27.50 ml, 0.12 mole) over a 30 minute period under a nitrogen atmosphere. The mixture was then stirred at 2° C. for one hour. The clear orange solution was diluted with methylene chloride (50 ml) and washed with water (3×200 ml) and then brine (100 ml), dried (Na$_2$SO$_4$) and evaporated, yielding 37.40 g (0.099 mole, yield 99%) of the title compound as a yellow solid: $^1$Hmr (CDCl$_3$, EM-360A, 60 MHz) δ: 0.26 (6H, s, Si(CH$_3$)$_2$), 0.96 (9H, s, SiC(CH$_3$)$_3$), 4.25 (1H, d, J=2.5 Hz, 4-H), 4.97 (1H, d, J=2.5 Hz, 4-H), 5.32 (2H, s, —CO$_2$CH$_2$Ar), 7.48 (2H, "d", J=9.0 Hz, ArH's) and 8.22 ppm (2H, "d", J=9.0 Hz, ArH's); ir (film) $\nu_{max}$: 2090 (N$_2$), 1694 (ester), 1600 (C=C) and 1344 cm$^{-1}$ (NO$_2$).

EXAMPLE 3

General Procedure for Preparation of
2-Diazo-3-trimethylsilyloxy-3-butenoic acid ester

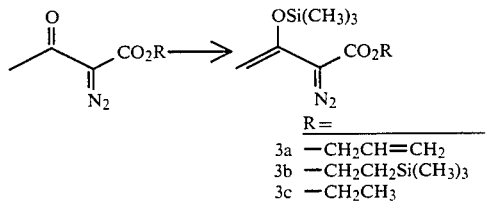

| R = | |
|---|---|
| 3a | —CH$_2$CH=CH$_2$ |
| 3b | —CH$_2$CH$_2$Si(CH$_3$)$_3$ |
| 3c | —CH$_2$CH$_3$ |

To a stirred solution of α-diazoacetoacetic acid esters, allyl, trimethylsilylethyl and ethyl, (1 mmol) and triethylamine (0.20 mL, 1.4 mmol) in dry CH$_2$Cl$_2$ or CCl$_4$ (2 mL) was added at 0°–5° C. trimethylsilyl trifluoromethanesulfonate (0.22 mL, 1.1 mmol; Aldrich) under a dry nitrogen atmosphere and the mixture stirred (0°–5°, N$_2$) for 30 min. To this clear yellow solution was added anhydrous hexanes (5 ml) followed by stirring for 10 min under a nitrogen atmosphere. After removing the oily deposit by gravity filtration, the hexanes solution was evaporated in vacuo and the residue was redissolved in anhydrous hexanes (10 ml). The insoluble material was again removed by gravity filtration and the filtrate was evaporated in vacuo to obtain as yellow crystals or 3a, b, and c as orangish oil in 77–97% yield. The whole operation should be performed under an anhydrous atmosphere since the products are sensitive to moisture.

3a: (allyl ester): 77% yield: ir (neat)$\nu_{max}$: 2100 (C=N$_2$), 1710 (ester), and 1605 (C=C) cm$^{-1}$; $^1$Hmr (CCl$_4$)δ: 0.20 (9H, s, SiMe$_3$), 4.15 (1H, d, J=2 Hz, vinyl proton), 4.63 (2H, d, J=5 Hz, CO$_2$CH$_2$), 4.95 (1H, d, J=2 Hz, vinyl proton), and 5–6.2 (3H, m, vinyl protons) ppm.

(trimethylsilyl-ethyl ester): 97% yield; ir (neat$\nu_{max}$: 2090 (C=N$_2$), 1705 (ester), and 1605 (C=C) cm$^{-1}$; $^1$Hmr (CCl$_4$) δ: 0.07 (9H, s, SiMe$_3$), 0.25 (9H, s, OSiMe$_3$), 1.00 (2H, 't', J=8 Hz, CH$_2$Si), 4.15 (1H, d, J=2 Hz, vinyl proton), 4.23 (2H, 't' J=8 Hz, CO$_2$CH$_2$), 4.98 (1H, d, J=2 Hz, vinyl proton) ppm.

(ethyl ester): 78% yield; ir (neat)$\nu_{max}$: 2090 (C=N$_2$) 1710 (ester), and 1605 (C=C) cm$^{-1}$; $^1$Hmr (CCl$_4$)δ: 0.25 (9H, s, SiMe$_3$), 1.32 (3H, t, J=7 Hz, CH$_3$), 4.17 (1H, d, J=2 Hz, vinyl proton), 4.23 (2H, q, J=7 Hz, C$_3$), 4.17 (1H, d, J=2 Hz, vinyl proton) ppm.

EXAMPLE 4

General Procedure for Preparation of 2-Diazo-3-(tert-butyldimethylsilyloxy)-3-butenoic acid ester

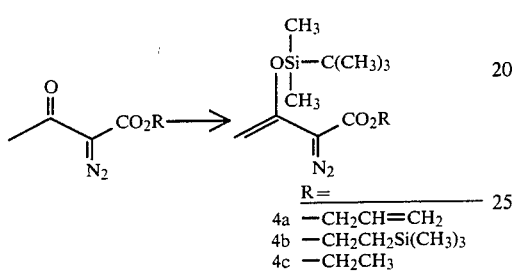

4a —CH$_2$CH=CH$_2$
4b —CH$_2$CH$_2$Si(CH$_3$)$_3$
4c —CH$_2$CH$_3$

To a stirred solution of α-diazoacetoacetic acid esters, allyl, trimethylsilylethyl and ethyl, (1 mmol) and triethylamine (0.20 mL, 1.4 mmol) in dry CH$_2$Cl$_2$ (2 mL) was added at 0°-5° C., tert-butyldimethylsilyl trifluoromethanesulfonate (0.28 mL, 1.2 mmol: Fluka) under a nitrogen atmosphere and the yellow mixture stirred at 0°-5° C. for 15 min. This was diluted with hexanes (20 mL), washed with a diluted NaHCO$_3$ solution and then brine, dried (Na$_2$SO$_4$) and evaporated to obtain 4a-4c as orangish oil in 93-99% yield.

4a (allyl ester): 96% yield; Rf 0.6 (20% EtOAc/Hex; partially decomposed to α-diazoacetate on the plate); ir (film)$\nu_{max}$: 2100 (C=N$_2$), 1715 (ester), and 1610 (C=C) cm$^{-1}$; uv (CH$_2$Cl$_2$)$\nu_{max}$: 280 nm (ε6000); $^1$Hmr (CDCl$_3$)δ: 0.23 (6H, s, SiMe$_2$), 0.93 (9H, s, si-tBu), 4.20 (1H, d, J=5 Hz, CO$_2$CH$_2$), 4.95 (1H, d, J=2 Hz, vinyl proton), and 5-6.3 (3H, m, vinyl proton) ppm.

4b (trimethylsilylethyl ester): 94% yield, Rf 0.7 (20% EtOAc/Hex); partially decomposed to α-diazoacetate on the plate); ir (film)$\nu_{max}$: 2100 (C=N$_2$), 1710 (ester) and 1610 (C=C) cm$^{-1}$; uv (CH$_2$Cl$_2$)λ$_{max}$: 280 nm (ε7600); $^1$Hmr (acetone d$_6$; CFT-20)δ: 0.06 (9H, s, SiMe$_3$), 0.25 (6H, s, SiMe$_2$), 0.94 (9H, s, Si-tBu), 1.05 (2H, t, J=8.3 Hz, CO$_2$CH$_2$CH$_2$SiMe$_3$), 4.31 (1H, d, J=1.8 Hz, vinyl proton) ppm.

4c (ethyl ester): 99% yield, Rf 0.66 (20% EtOAc/Hex; partially decomposed to α-diazoacetate on the plate); ir (film)$\nu_{max}$: 2090 (C=N$_2$), 1710 (ester), and 1610 (C=C) cm$^{-1}$; uv (CH$_2$Cl$_2$)λ$_{max}$: 282 nm (ε7950); $^1$Hmr (acetone-d$_6$; CFT-20)δ: 0.25 (6H, s, SiMe$_2$), 0.94 (9H, s, Si-tBu), 1.26 3H, t, J=7.1 Hz, CO$_2$CH$_2$CH$_3$); 4.25 (2H, q, J=7.1 Hz, CO$_2$CH$_2$CH$_3$), 4.28 (1H, d, J=1.9 Hz, vinyl proton) ppm.

EXAMPLE 5

Preparation of 1-p-Nitrobenzyloxycarbonyl-1-diazo-2-t-butyldimethyl-silyloxy-2-buten

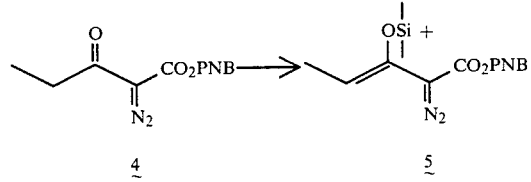

To a cooled (0°) solution of 54 g (0.2M) of compound 4 in 400 ml of CH$_2$Cl$_2$ was added 41.4 g (0.4M) of TEA followed by 56 g (0.21M) of t-butyldimethylsilyl chloride in 30 ml of CH$_2$Cl$_2$ over 40 min. The solution was stirred for 120 min, then washed with ice-water. The CH$_2$Cl$_2$ was dried (MgSO$_4$), filtered and evaporated in vacuo to give 68 g (89% yield) of compound 5 as yellow solids. m.p. 54°-55°. IR (KBr) γ2080 and 1695 cm$^{-1}$. The NMR of compound 5 indicated that compound 5 was obtained as a E/Z mixture at the olefinic position in a ratio of 9:1. NMR (CDCl$_3$ major isomer) δ0.15 (6H, s), 0.90 (9H, s), 1.58 (3H, d, J=7.0 Hz), 5.15 (2H, s), 7.30 (2H, d, J=9.0 Hz) and 8.0 (2H, d, J=9.0 Hz).

EXAMPLE 6

Following the general procedures of Examples 1-5 and substituting the appropriate starting materials, the following compounds may be prepared:

| R$^5$ | R$^6$ | R$^1$ | R$^2$ | R$^3$ | R$^7$ |
|---|---|---|---|---|---|
| H | H | isopropyl | isopropyl | isopropyl | p-nitrobenzyl |
| " | " | " | " | " | —CH$_2$CH=CH$_2$ |
| " | " | " | " | " | —CH$_2$CH=CHC$_6$H$_5$ |
| " | " | " | " | " | —CH$_2$CH=CHCO$_2$CH$_3$ |
| " | " | " | " | " | —CH$_2$C=CH$_2$<br>\|<br>Cl |
| " | " | " | " | " | —CH$_2$C=CH$_2$<br>\|<br>C$_6$H$_5$ |

-continued $$\underset{R^6}{\overset{R^5}{>}}C=\underset{R^3}{\overset{OSi-R^2}{\underset{CO_2R^7}{\overset{R^1}{|}}}}$$
(with =N₂ on the carbon bearing CO₂R⁷)

| R⁵ | R⁶ | R¹ | R² | R³ | R⁷ |
|---|---|---|---|---|---|
| " | " | " | " | " | —CH₂CH=CHCH₃ |
| " | " | " | " | " | —Si(C₆H₅)₂C(CH₃)₃ |
| " | " | " | " | " | —Si(CH(CH₃)₂)₃ |
| " | " | " | " | " | —CH₂CH₂Si(CH₃)₃ |
| " | " | " | " | " | —Si(CH₃)₂—O—[2,4,6-tri-t-butylphenyl] |
| CH₃ | " | " | " | " | p-nitrobenzyl |
| H | " | " | " | " | —CH₂CH=CH₂ |
| " | " | " | " | " | —CH₂CH=CHC₆H₅ |
| " | " | " | " | " | —CH₂CH=CHCO₂CH₃ |
| " | " | " | " | " | —CH₂C(Cl)=CH₂ |
| " | " | " | " | " | —CH₂C(C₆H₅)=CH₂ |
| " | " | " | " | " | —CH₂CH=CHCH₃ |
| " | " | " | " | " | —Si(C₆H₅)₂C(CH₃)₃ |
| " | " | " | " | " | —Si(CH(CH₃)₂)₃ |
| " | " | " | " | " | —CH₂CH₂Si(CH₃)₃ |
| " | " | " | " | " | —Si(CH₃)₂—O—[2,4,6-tri-t-butylphenyl] |
| " | " | C₆H₅ | t-butyl | C₆H₅ | p-nitrobenzyl |
| " | " | " | " | " | —CH₂CH=CH₂ |
| " | " | " | " | " | —CH₂CH=CHC₆H₅ |
| " | " | " | " | " | —CH₂CH=CHCO₂CH₃ |
| " | " | " | " | " | —CH₂C(Cl)=CH₂ |

-continued
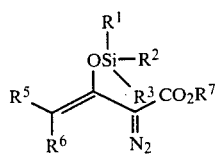
| R$^5$ | R$^6$ | R$^1$ | R$^2$ | R$^3$ | R$^7$ |
|---|---|---|---|---|---|
| " | " | " | " | " | $-CH_2C(C_6H_5)=CH_2$ |
| " | " | " | " | " | $-CH_2CH=CHCH_3$ |
| " | " | " | " | " | $-Si(C_6H_5)_2C(CH_3)_3$ |
| " | " | " | " | " | $-Si(CH(CH_3)_2)_3$ |
| " | " | " | " | " | $-CH_2CH_2Si(CH_3)_3$ |
| " | " | " | " | " | $-Si(CH_3)_2-O-C_6H_2(C(CH_3)_3)_3$ |
| CH$_3$ | " | " | " | " | p-nitrobenzyl |
| H | " | " | " | " | $-CH_2CH=CH_2$ |
| " | " | " | " | " | $-CH_2CH=CHC_6H_5$ |
| " | " | " | " | " | $-CH_2CH=CHCO_2CH_3$ |
| " | " | " | " | " | $-CH_2C(Cl)=CH_2$ |
| " | " | " | " | " | $-CH_2C(C_6H_5)=CH_2$ |
| " | " | " | " | " | $-CH_2CH=CHCH_3$ |
| " | " | " | " | " | $-Si(C_6H_5)_2C(CH_3)_3$ |
| " | " | " | " | " | $-Si(CH(CH_3)_2)_3$ |
| " | " | " | " | " | $-CH_2CH_2Si(CH_3)_3$ |
| " | " | " | " | " | $-Si(CH_3)_2-O-C_6H_2(C(CH_3)_3)_3$ |

-continued $$\begin{array}{c} R^1 \\ | \\ OSi-R^2 \\ R^5 \diagdown \quad | \\ \phantom{R^5}C=C-R^3\quad CO_2R^7 \\ R^6 \phantom{=C} \| \\ \phantom{R^6===}N_2 \end{array}$$

| $R^5$ | $R^6$ | $R^1$ | $R^2$ | $R^3$ | $R^7$ |
|---|---|---|---|---|---|
| " | " | $CH_3$ | $C(CH_3)_3$ <br> —O—⟨2,4,5-tri-$C(CH_3)_3$-phenyl⟩ | $CH_3$ | p-nitrobenzyl |
| " | " | " | " | " | $-CH_2CH=CH_2$ |
| " | " | " | " | " | $-CH_2CH=CHC_6H_5$ |
| " | " | " | " | " | $-CH_2CH=CHCO_2CH_3$ |
| " | " | " | " | " | $-CH_2\underset{Cl}{C}=CH_2$ |
| " | " | " | " | " | $-CH_2\underset{C_6H_5}{C}=CH_2$ |
| " | " | " | " | " | $-CH_2CH=CHCH_3$ |
| " | " | " | " | " | $-\underset{C_6H_5}{\overset{C_6H_5}{Si}}-C(CH_3)_3$ |
| " | " | " | " | " | $-\underset{CH(CH_3)_2}{\overset{CH(CH_3)_2}{Si}}-CH(CH_3)_2,$ |
| " | " | " | " | " | $-CH_2CH_2Si(CH_3)_3$ |
| " | " | " | " | " | $-\underset{CH_3}{\overset{CH_3}{Si}}-O-\text{(2,4,5-tri-}C(CH_3)_3\text{-phenyl)}$ |
| $CH_3$ | " | " | " | " | p-nitrobenzyl |
| H | " | " | " | " | $-CH_2CH=CH_2$ |
| " | " | " | " | " | $-CH_2CH=CHC_6H_5$ |
| " | " | " | " | " | $-CH_2CH=CHCO_2CH_3$ |
| " | " | " | " | " | $-CH_2\underset{Cl}{C}=CH_2$ |
| " | " | " | " | " | $-CH_2\underset{C_6H_5}{C}=CH_2$ |
| " | " | " | " | " | $-CH_2CH=CHCH_3$ |
| " | " | " | " | " | $-\underset{C_6H_5}{\overset{C_6H_5}{Si}}-C(CH_3)_3$ |
| " | " | " | " | " | $-\underset{CH(CH_3)_2}{\overset{CH(CH_3)_2}{Si}}-CH(CH_3)_2,$ |

-continued

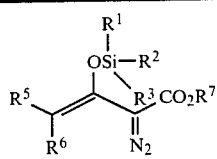

| R⁵ | R⁶ | R¹ | R² | R³ | R⁷ |
|---|---|---|---|---|---|
| " | " | " | " | " | —CH₂CH₂Si(CH₃)₃ |
| " | " | " | " | " | —Si(CH₃)₂—O—[2,4,6-tri-t-butylphenyl] |
| CH₃ | CH₃ | " | t-butyl | " | p-nitrobenzyl |
| H | H | " | " | " | —CH₂CH=CH₂ |
| " | " | " | " | " | —CH₂CH=CHC₆H₅ |
| " | " | " | " | " | —CH₂CH=CHCO₂CH₃ |
| " | " | " | " | " | —CH₂C(Cl)=CH₂ |
| " | " | " | " | " | —CH₂C(C₆H₅)=CH₂ |
| " | " | " | " | " | —CH₂CH=CHCH₃ |
| " | " | " | " | " | —Si(C₆H₅)₂C(CH₃)₃ |
| " | " | " | " | " | —Si(CH(CH₃)₂)₃ |
| " | " | " | " | " | —CH₂CH₂Si(CH₃)₃ |
| " | " | " | " | " | —Si(CH₃)₂—O—[2,4,6-tri-t-butylphenyl] |
| CH₃ | CH₃ | " | CH₃ | " | p-nitrobenzyl |
| H | H | " | " | " | —CH₂CH=CH₂ |
| " | " | " | " | " | —CH₂CH=CHC₆H₅ |
| " | " | " | " | " | —CH₂CH=CHCO₂CH₃ |
| " | " | " | " | " | —CH₂C(Cl)=CH₂ |
| " | " | " | " | " | —CH₂C(C₆H₅)=CH₂ |
| " | " | " | " | " | —CH₂CH=CHCH₃ |
| " | " | " | " | " | —Si(C₆H₅)₂C(CH₃)₃ |

-continued

| R⁵ | R⁶ | R¹ | R² | R³ | R⁷ |
|---|---|---|---|---|---|
| " | " | " | " | " | CH(CH₃)₂<br>    |<br>—Si—CH(CH₃)₂,<br>    |<br>CH(CH₃)₂ |
| " | " | " | " | " | —CH₂CH₂Si(CH₃)₃ |
| " | " | " | " | " | CH₃<br>|<br>—Si—O—(2,4,6-tri-tert-butylphenyl)<br>|<br>CH₃ |

EXAMPLE 7

Preparation of (3S,4S)-3-[(1R)-Hydroxyethyl]-4-[3-(4-nitrobenzyloxy)-carbonyl-2-oxo-3-diazopropyl]azetidin-2-one

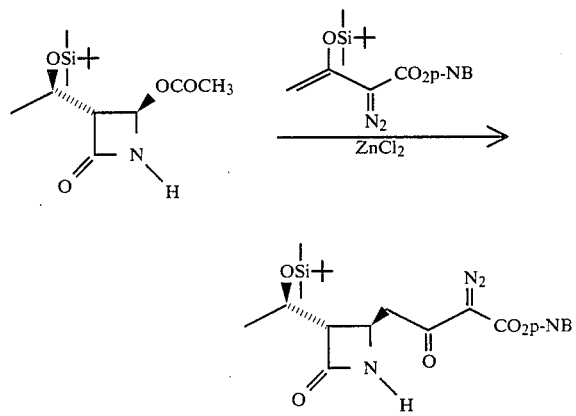

To a suspension of anhydrous zinc chloride (34 mg, 0.25 mmole), in methylene chloride (2 ml) was added a solution of 1′R,3R,4R)-3-(1′-tert-butyldimethylsilyloxyethyl)-4-acetoxyazetidin-2-one (144 mg, 0.5 mmole) in methylene chloride (4 ml) followed by solid 4-nitrobenzyl-2-diazo-3-tert-butyldimethylsilyloxy-3-butenoate (350 mg, 0.93 mole) under a nitrogen atmosphere. The mixture was stirred at room temperature under nitrogen for 4.5 hours. The mixture, diluted with ethyl acetate (50 ml), was washed with saturated sodium bicarbonate (2×25 ml) and then brine (30 ml), dried (Na₂SO₄) and evaporated, yielding a crude oily yellow solid which was purified by column chromatography [(SiO₂, 30 g) eluted with methylene chloride:ethyl acetate 4:1] to obtain 198 mg (0.405 mmole, 81%) of the title compound as an oil identical (tlc, ¹Hmr) with an authentic sample prepared by a published procedure.

EXAMPLE 8

Preparation of (3S,4R)-3-[(1R)-Hydroxyethyl]-4-[3-(4-nitrobenzyloxy)carbonyl-2-oxo-3-diazopropyl]azetidin-2-one

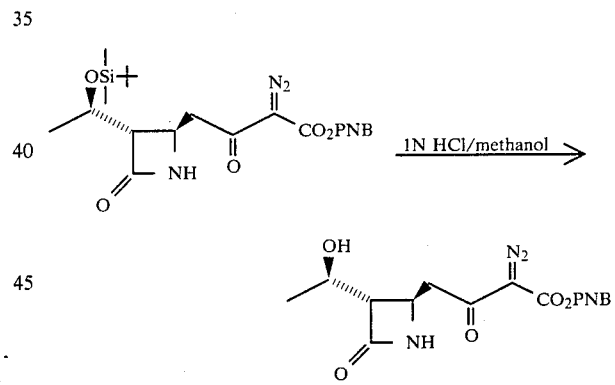

To a solution of (3S,4R)-3-[(1R)-(tert-butyldimethylsilyloxy)ethyl]-4-[3-(4-nitrobenzyloxy)carbonyl-2-oxo-3-diazopropyl]azetidin-2-one (72 mg, 0.15 mmole) in methanol (1.0 ml) was added 1N aqueous HCl (0.2 ml) and the mixture was stirred at room temperature for 2 hours by which time tlc (ethyl acetate) indicated that the reaction was completed. During this period the title compound was precipitated. This was filtered and rinsed with cold CH₃OH-H₂O (9:1) and then cold diethyl ether to obtain 43 mg (0.11 mmole, yield 73%) of the title compound as a white solid. The title compound was similarly obtained from (3S,4R)-3-{(1R)-[(2,4,6-tri-tert-butylphenoxy)dimethylsilyloxy]ethyl}-4-[3-(4-nitrobenzyloxy)carbonyl-2-oxo-3-diazopropyl]azetidin-2-one.

EXAMPLE 9

Preparation of (3S,4R)-3-{(1R-[(2,4,6-Tri-tert butylphenoxy)dimethylsilyloxy]ethyl}-4-[3-(4-nitrobenzyl)oxycarbonyl-2-oxo-3-diazopropyl]azetidin-2-one

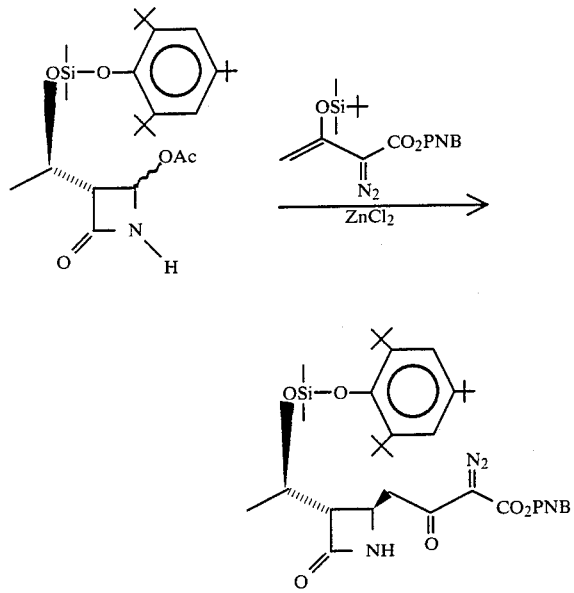

The title compound was prepared in 84% yield from (3R,4R and 4S)-4-acetoxy-3-{(1R-[(2,4,6-tri-tert-butyl-phenoxy)dimethylsilyloxy]ethyl}-2-azetidinone by the method described above for the corresponding t-butyl dimethylsilyl derivative:

$^1$Hmr (CDCl$_3$, 80 MHz)δ: 0.26 (3H, s, SiMe), 0.40 (3H, s, SiMe), 1.27 (9H, s, t-Bu), 1.41 (18H, s, (t-Bu)$_2$), 2.92 (1H, dd, J$_{3-1'}$=4.7 Hz, J$_{3-4}$=2.5 Hz, 3-H), 2.97 (1H, dd, J$_{gem}$=17.6 Hz, J$_{1''b-4}$=9.6 Hz, 1''-H$_b$), 3.40 (1H, dd, J$_{gem}$=17.6 Hz, J$_{1''a-4}$=3.5 Hz, 1''-H$_a$), 3.98-4.24 (1H, m, 4-H), 4.32-4.57 (1H, m, 1'-H), 5.35 (2H, s, —CO$_2$CH$_2$Ar), 5.95 (1H, br s, NH), 7.22 (2H, s, ArH's of the ether), 7.52 (2H, "d", J=8.7 Hz, ArH's of the ester) and 8.25 ppm (2H, "d", J=8.7 Hz, ArH's of the ester): ir (neat)ν$_{max}$: 3300 (br, NH), 2137 (—N$_2$), 1755 (β-lactam), 1720 (ester), 1651 (C=O), 1523 and 1345 cm$^{-1}$ (NO$_2$).

EXAMPLE 10

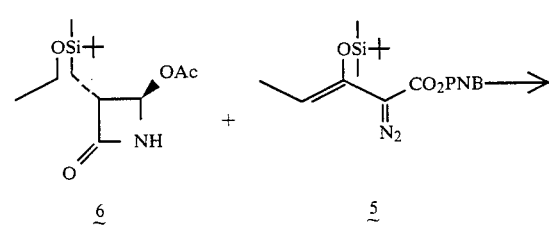

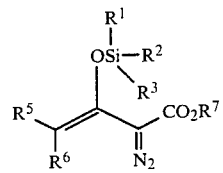

4β-1-Methyl-3-diazo-3-p-nitrobenzyloxycarbonyl-2-oxo-propyl)-3α-[1-(R)-t-butyldimethylsilyloxy ethyl]-azetidin-2-one To a suspended solution of 12.5 g (0.1M) of anhydrous ZnCl$_2$ in 700 ml of CH$_2$Cl$_2$ was added 60.4 g (0.21M) of compound 6 and stirred for 15 min at 23° then cooled to 0°. A solution of 106 g (0.27M) of compound 5 in 200 ml of CH$_2$Cl$_2$ was added dropwise to the above reaction solution over 90 min, then stirred for 120 min without the cooling bath. The reaction mixture was washed with aq. NaHCO$_3$ (4×150 ml), water, brine and dried (MgSO$_4$). Evaporation of dried solvent gave a dark oil, which was purified by SiO$_2$ column; elution of the column with EtOAc-CH$_2$Cl$_2$ (1:9) gave 51.5 g (54%) of compound 7 as a white crystalline material, m.p. 112°-114°. IR (KBr) γ2130,1760 and 1720 cm$^{-1}$. The 360 MHz nmr of compound 7 indicated that compound 7 was obtained as a mixture at the 1-methyl position in a ratio of 2:1. NMR (CDCl$_3$) δ0.3 -0.6 (6H, 2s), 0.8 Z (9H, 2s), 1.05-1.15 (6H, m), 2.68 (0.66H, q, J=6.6 and 2.0 Hz), 2.88 (0.34, q, J=6.6 and 2.0 Hz) 3.57 (1H, m), 3.84 (1H, m), 4.09 (1H, m). 517 (2H, twos), 5.84 (0.66H, s), 5.95 (0.34H, s), 7.52 (2H, d, J=8.5 Hz) and 8.23 (2H, d, J=8.5 Hz).

We claim:

1. A process for the preparation of a compound of the formula

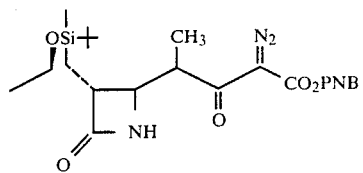

wherein R$^5$ and R$^6$ are each independently hydrogen or methyl, R$^7$ is an ester group selected from C$_1$-C$_4$ alkyl, p-nitrobenzyl, —CH$_2$CH=CH$_2$, —CH$_2$CH=CHC$_6$H$_5$, —CH$_2$CH=CHCO$_2$CH$_3$,

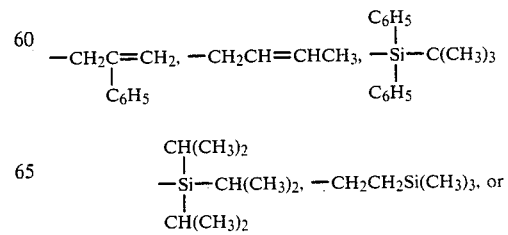

-continued

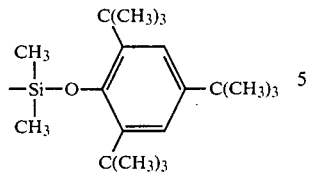

and $R^1$, $R^2$ and $R^3$ are each independently $C_1$-$C_4$ alkyl or, alternatively,

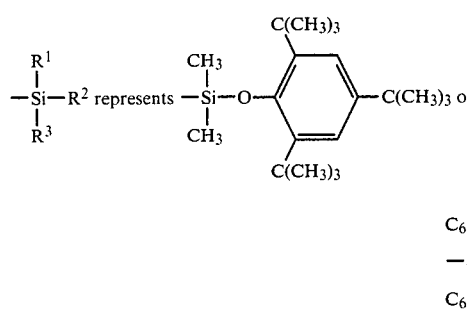

which process comprises reacting a compound of the formula

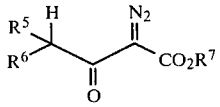 IV wherein $R^5$, $R^6$, and $R^7$ are as defined above with a silyl triflate of the formula

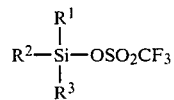 V wherein $R^1$, $R^2$, and $R^3$ are as defined above in an inert solvent and in the presence of an organic base.

2. The process according to claim 1 wherein the reaction is carried out at a temperature of from about $-40°$ C. to $+30°$ C.

3. The process according to claim 1 or claim 2 wherein the organic base is a $C_1$-$C_4$ trialkylamine and the solvent is methylene chloride.

* * * * *

UNITED STATES PATENT AND TRADEMARK OFFICE
CERTIFICATE OF CORRECTION

PATENT NO. : 4,683,296
DATED : July 28, 1987
INVENTOR(S) : Yasutsugu Ueda, et al.

It is certified that error appears in the above-identified patent and that said Letters Patent is hereby corrected as shown below:

In Claim 1, column 30, line 57, after "$-CH_2CH=CHCO_2CH_3$", there should be added the group -- $-CH_2\underset{Cl}{C}=CH_2$ -- which was omitted.

Signed and Sealed this

Twenty-fourth Day of November, 1987

Attest:

DONALD J. QUIGG

Attesting Officer

Commissioner of Patents and Trademarks